United States Patent [19]
Zinreich

[11] Patent Number: 5,795,335
[45] Date of Patent: Aug. 18, 1998

[54] INTRAVENOUS TUBE RESTRAINT AND COVER DEVICE

[76] Inventor: Eva S. Zinreich, 10 Stream Ct., Owing Mills, Md. 21117

[21] Appl. No.: 806,833

[22] Filed: Feb. 26, 1997

[51] Int. Cl.$^6$ .................................................. A61M 5/32
[52] U.S. Cl. ................................ 604/174; 128/DIG. 26; 128/2
[58] Field of Search ........................ 604/174, 180, 604/179; 128/DIG. 26

[56] References Cited

U.S. PATENT DOCUMENTS

| | | | |
|---|---|---|---|
| 2,669,231 | 2/1954 | Fisher | 128/214 |
| 3,288,136 | 11/1966 | Lund | 128/133 |
| 3,430,300 | 3/1969 | Doan | 24/73 |
| 3,677,250 | 7/1972 | Thomas | 128/348 |
| 3,726,280 | 4/1973 | Lacount | 128/349 R |
| 3,782,383 | 1/1974 | Thompson | 128/214 |
| 3,826,254 | 7/1974 | Mellor | 128/133 |
| 3,834,380 | 9/1974 | Boyd | 128/133 |
| 3,878,849 | 4/1975 | Muller | 128/349 R |
| 3,972,321 | 8/1976 | Proctor | 128/348 |
| 3,990,454 | 11/1976 | Schlesinger | 128/349 R |
| 4,074,397 | 2/1978 | Rosin | 24/73 AS |
| 4,088,136 | 5/1978 | Hasslinger | 128/349 R |
| 4,096,863 | 6/1978 | Kaplan et al. | 128/349 R |
| 4,120,304 | 10/1978 | Moor | 128/348 |
| 4,129,128 | 12/1978 | McFarlane | 128/133 |
| 4,149,535 | 4/1979 | Volder | 128/214.4 |
| 4,161,177 | 7/1979 | Fuchs | 128/214.4 |
| 4,164,943 | 8/1979 | Hill et al. | 128/348 |
| 4,165,748 | 8/1979 | Johnson | 128/348 |
| 4,333,468 | 6/1982 | Geist | 128/348 |
| 4,392,853 | 7/1983 | Muto | 604/171 |
| 4,416,664 | 11/1983 | Womack | 604/174 |
| 4,419,097 | 12/1983 | Rowland | 604/174 |
| 4,445,894 | 5/1984 | Kovacs | 604/179 |
| 4,484,914 | 11/1984 | Brown | 604/180 |
| 4,519,793 | 5/1985 | Galindo | 604/180 |
| 4,569,348 | 2/1986 | Hasslinger | 604/179 |
| 4,571,245 | 2/1986 | Hubbard et al. | 604/179 |
| 4,591,356 | 5/1986 | Christie | 604/179 |
| 4,617,017 | 10/1986 | Hubbard et al. | 604/179 |
| 4,645,492 | 2/1987 | Weeks | 604/174 |
| 4,648,391 | 3/1987 | Ellis | 128/132 R |
| 4,678,462 | 7/1987 | Vaillancourt | 604/180 |
| 4,700,432 | 10/1987 | Fennell | 24/16 R |
| 4,702,736 | 10/1987 | Kalt et al. | 604/180 |
| 4,726,716 | 2/1988 | McGuire | 604/180 |
| 4,898,587 | 2/1990 | Mera | 604/174 |
| 4,962,757 | 10/1990 | Stefan | 128/DIG. 26 |
| 4,976,698 | 12/1990 | Stokley | 604/174 |
| 5,000,741 | 3/1991 | Kalt | 604/180 |
| 5,019,050 | 5/1991 | Lynn et al. | 604/179 |
| 5,100,393 | 3/1992 | Johnson | 604/180 |
| 5,147,320 | 9/1992 | Reynolds et al. | 604/174 |
| 5,147,322 | 9/1992 | Bowen et al. | 604/180 |
| 5,226,892 | 7/1993 | Boswell | 604/180 |
| 5,292,312 | 3/1994 | Delk et al. | 604/180 |
| 5,304,146 | 4/1994 | Johnson et al. | 604/180 |
| 5,354,282 | 10/1994 | Bierman | 604/180 |
| 5,364,368 | 11/1994 | Kauffman et al. | 604/180 |
| 5,370,627 | 12/1994 | Conway | 604/180 |
| 5,372,589 | 12/1994 | Davis | 604/180 |
| 5,395,344 | 3/1995 | Beisang, III et al. | 604/180 |
| 5,415,647 | 5/1995 | Pisarik | 604/115 |
| 5,449,349 | 9/1995 | Sallee et al. | 604/180 |

*Primary Examiner*—Gary Jackson
*Attorney, Agent, or Firm*—Oldham & Oldham Co., LPA

[57] ABSTRACT

A restraint for securing and protecting medical tubing. The restraint device is comprised of an anchor plate having an outer surface and an inner surface. The anchor plate also includes a receiver upon which a means for retaining tubing is connected. The retaining means has a tube clamping portion which holds the tubing and an anchoring portion which secures the retaining means to the anchor plate. The device can preferably be non-adhesively positioned in an area of the patient's body through a fastening means located on the anchor plate. In addition, a cover is connected to the anchor plate for protecting and further securing medical tubing. The all-plastic device can be cleaned, sanitized and reused if desired.

19 Claims, 2 Drawing Sheets

INTRAVENOUS TUBE RESTRAINT AND COVER DEVICE

TECHNICAL FIELD

This invention relates generally to devices used to retain catheters and other medical tubing in place, and more particularly, to such devices which protect retained catheters and other medical tubing from damage or contamination with a protective cover.

BACKGROUND OF THE INVENTION

It is common practice in a number of medical disciplines to transport gases or liquids to and from a patient's body through generally tubular items such as catheters, infusion tubes, cannulae and naso-gastric tubing. Certain procedures require that the fluids be delivered only in preferred veins. For example, the intravenous administration of highly concentrated solutions such as those required to deliver nutrients in sufficient quantities to achieve tissue synthesis and anabolism, also known as total parenteral nutrition, is carried out by way of the subclavian vein where it can be properly diluted by the large volume of blood available. In addition to concerns of location, intravenous treatment and/or support of patients commonly requires the simultaneous use of multiple tubular items with the accompanying dangers of accidental detachment or entangling of the tubing. To avoid these dangers and to maintain tubing in the vicinity of the desired position, tubes and wires have traditionally been secured to the patient's skin or clothing by adhesive tape, however this method has proven unsatisfactory in terms of patient mobility and comfort. To maintain the necessary restraint and overcome the discomfort and irritation associated with the removal of adhesive tape from a patient's skin, various types of alternative securing devices have been developed.

One class of device which has been developed comprises a strap which can be encircled and fastened about a patient's limb providing a support for securing a tube or similar item. For example, U.S. Pat. No. 5,019,050 to Lynn discloses a catheter securing device incorporating a strap which is wrapped about a limb and fastened with a separable hook and loop-type fastener. A second flexible strap member is then adhered about a catheter tube and secured to the first strap. The device is convenient, however, keeping the strap taut can be uncomfortable and may restrict blood flow. In addition, the device is further limited to those areas of the body where a limb is accessible and where securing the tubing to a limb is practicable in terms of the particular treatment being administered.

There are a number of catheter restraints of the type comprising a substrate wherein one surface is coated with an adhesive for applying the device to the skin or clothing of the patient and the other surface includes various catheter restraint means such as retaining tabs (U.S. Pat. No. 5,147,322 to Bowen), clamping tubes (U.S. Pat. No. 3,834,380 to Boyd) and flexible straps (U.S. Pat. No. 4,333,468 to Geist). These devices are typically able to accommodate a single tube or catheter. Moreover, the absence of a protective cover allows the tubing to become accidentally detached and exposes it to external impact and/or contamination.

U.S. Pat. No. 5,226,892 to Boswell discloses a surgical tubing clamp having hinged opposing plates which contain foam pads for frictionally gripping, without crimping or crushing, delicate surgical tubing of varying diameter such as fiber optic tubing. The disposable device is adhesively attached to a surgical drape, a number of tubes of varying diameter may then be placed on the lower foam pad and the upper pad closed about the hinge and shut with a snap latch thereby securing and covering the tubing. The device is of particular value both for its safe clamping of delicate surgical tubing and for its application to a variety of tubing diameters. However, the foam pads are absorbent and may act as a sponge for fluids such as blood and intervenous fluids. Consequently, the device is susceptible to the collection of potential contaminants and is not reusable.

Despite the advances in devices directed toward conveniently restraining medical tubing in relation to the needs of the patient, there is a need for a device which can adequately restrain tubing, without the use of adhesives, particularly to areas about the neck, shoulders and upper torso. The present state of the art does not permit such a non-adhesive restraint by a reusable device capable of protecting the tubing from both damage and contamination.

SUMMARY OF THE INVENTION

The invention disclosed and claimed herein is a restraint for securing and protecting medical tubing. The restraint device is comprised of an anchor plate having an outer surface and an inner surface. The anchor plate also includes a receiver upon which a means for retaining tubing is connected. The retaining means has a tube clamping portion which holds the tubing and an anchoring portion which secures the retaining means to the anchor plate. The device can preferably be non-adhesively positioned in an area of the patient's body through a fastening means located on the anchor plate. In addition, a cover is connected to the anchor plate for protecting and further securing medical tubing.

A particular advantage of this form of intravenous tube restraint is that it accomplishes both the positioning of medical tubing at a desired location and the protecting of medical tubing from damage and contamination without the use of an adhesive or a strap. The device is adequately positioned by means attached to the device, such as a chain or a pin, so that it may be suspended about the neck of a patient or pinned to a patient's garment. The device is made entirely of plastic and can accommodate multiple diameters or types of tubing simultaneously. Because the device includes a cover, an additional means for holding the tubing in place is available by simply closing the lid. The cover also serves as a means for preventing the tubing from collecting dust or becoming entangled with other tubing and/or wiring.

It is thus an object of this invention to disclose a device for securing and protecting medical tubing which provides a novel means for positioning medical tubing to a convenient position on the patient's body where the treatment is administered.

It is a further object of this invention to provide a device for securing and protecting medical tubing capable of accommodating, simultaneously, multiple tubing diameters and/or tubing transporting multiple treatment fluids.

It is a further object of this invention to disclose a device for securing and protecting medical tubing which includes a cover means which can be closed over the device to protect and further secure the tubing.

It is a further object of this invention to disclose a device for securing and protecting medical tubing which is composed entirely of a non-absorbent material, such as plastic, which can easily be washed, sanitized and reused.

Other objects and advantages of this invention can be seen more clearly and will become apparent from the accompanying drawings and the following detailed description of the preferred embodiment.

DETAILED DESCRIPTION OF THE PREFERRED EMBODIMENT

Figure 1:
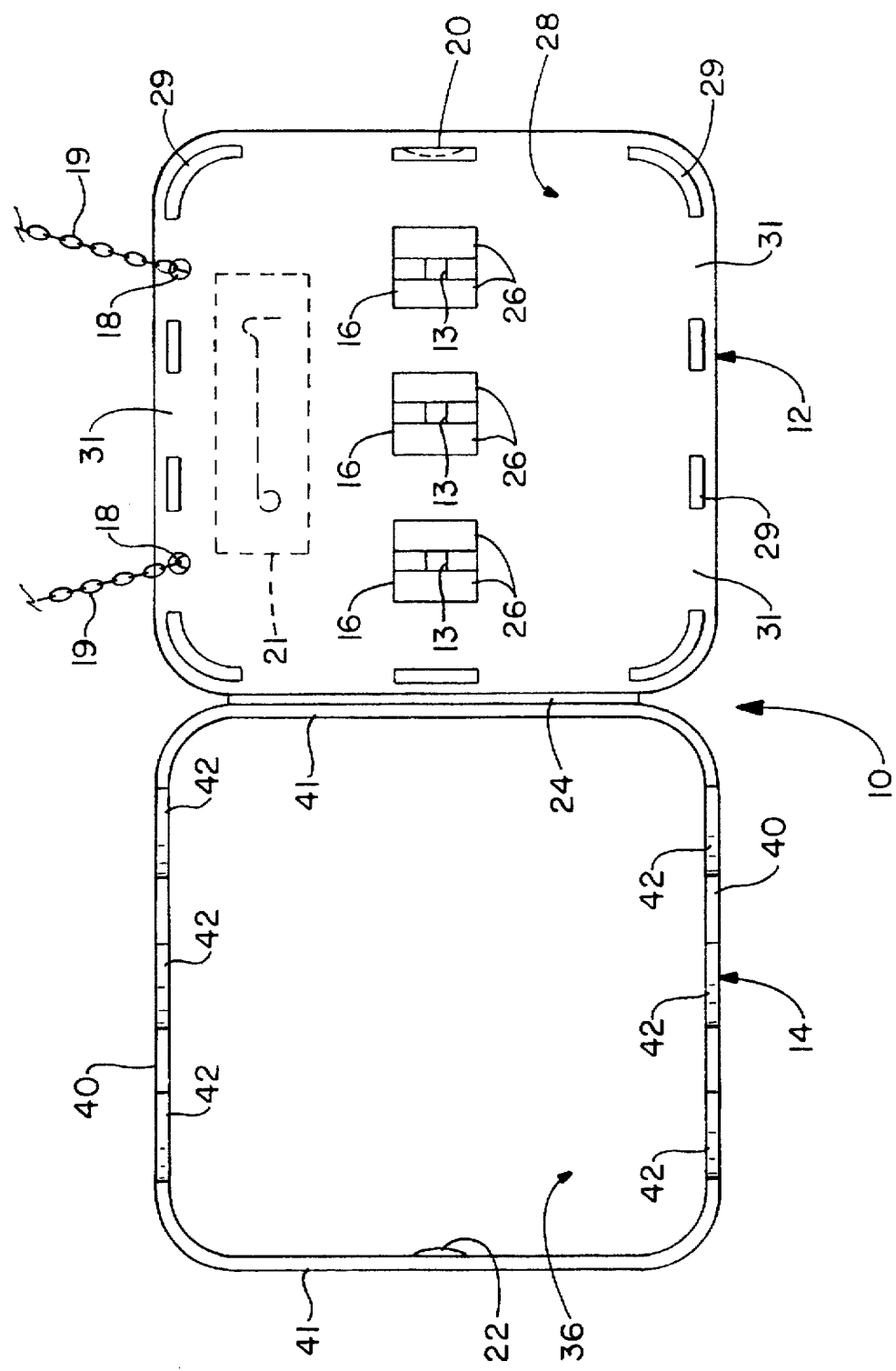
FIG. 1 is a top view of the present invention in its fully opened configuration.

An intravenous tube holder in accordance with the preferred embodiment of the present invention is indicated generally at 10 of FIG. 1. Anchor plate 12 having an inner surface 28 and a outer surface 30 provides a foundation for anchoring retaining clips 16. As explained below, the retaining clips 16 are anchored to the anchor plate 12 through a receiver such as slits 13. A cover 14 having an inner surface 36 and an outer surface 38 adjoins anchor plate 12 along a common edge and is connected by hinge 24. Hinge 24 provides a means by which cover 14 is held in opposed juxtaposition to anchor plate 12 so that when the cover 14 is closed over anchor plate 12 they form a clamshell-type structure. The structure is held in its closed configuration by a latch 22 positioned on cover 14 and a corresponding catch 20 positioned on anchor plate 12. Holes 18 through anchor plate 12 provide a means for passing a chain 19 or pin through the device for suspending the device around the neck or pinning to the garment of the patient.

In order for the cover 14 to rotate about the hinge 24 and close in its intended manner, the cover 14 and anchor plate 12 should have substantially the same cross sectional shape. In a preferred embodiment the cover 14 and anchor plate 12 are rectangular in cross section, although it should be clear to those skilled in the art that other cross sectional shapes can facilitate the desired closing of the cover 14 over the anchor plate 12.

Figure 2:
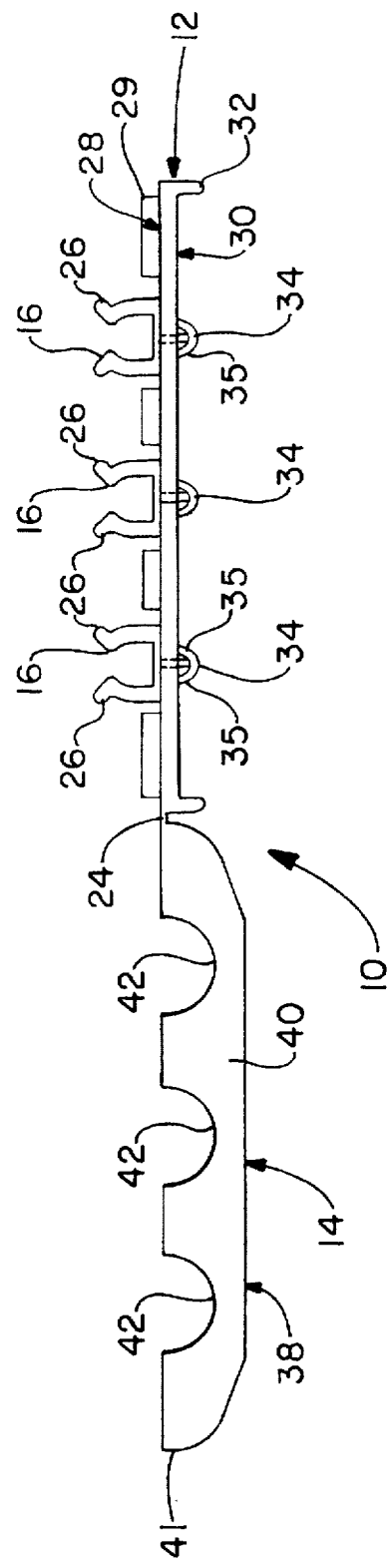
FIG. 2 is a side elevation view of the present invention in its fully opened configuration.

Retaining clips 16 are intended to engage and hold tubing such as intravenous tubing in a manner such that the tubing is engaged by the clips 16 and held with the tubing running parallel to the axis of the hinge 24. As best shown in FIG. 2, the retaining clips 16 are comprised of two resilient retaining clip arms 26 of predetermined spacing and a retaining clip anchor 34. The retaining clip anchor 34 is further comprised of a pair of compressible or resilient wings 35. The retaining clip 16 is secured to the anchor plate 12 by passing the retaining clip anchor 34 through a receiver such as slit 13 forcing the wings 35 to compress and later return to their expanded configuration after passing through the slit 13 thereby anchoring the clip 16 to the plate 12. The anchor plate 12 also includes a lip 32 extending from outer surface 30 which prevents the clip anchor 34 from protruding into the patient's body. To accomplish this it is significant that the dimension of the lip (width) be greater than length of anchor 34 protruding through slit 13. The two retaining clip arms 26, which when anchored comprise the portion of each clip 16 extending from the inner surface 28 of anchor plate 12, extend substantially perpendicular to the plane of the anchor plate 12, however in their most preferred embodiment the arms 26 form an elbow or dog's leg motif at their ends. The bending of the ends in this way creates a U-shaped channel which helps to retain the tubing by preventing the tubing from disengaging from the retaining clips 16. The arms 26 are preferably resilient so that they spread apart to allow tubing to pass through the elbows then retract when the tubing is within the U-shaped channel. To accomplish a firm retaining of the tubing without crushing or pinching, the opening created by the U-shaped channel is preferably slightly larger than the diameter of the tubing.

It is envisioned that the location, number and/or size of retaining clips 16 situated on anchor plate 12 could vary to accommodate particular medical applications. By altering the location and/or number of slits 13, retaining clips 16 can be anchored into a chosen location or, as an alternative, omitted as desired. To accommodate varying diameters of tubing, the size and spacing of retaining clip arms 26 can be modified. It is illustrated that one clip 16 is used to retain each tube, however it is envisioned that any number is possible. It is also anticipated that the retaining clips 16 can be color-coded to indicate tube diameter and/or the type of product being administered to the patient.

The periphery of anchor plate 12 has a rim 29, broken to create openings 31, which permit the secured tubing to pass unobstructed from the retaining device. The width of opening 31 is substantially the width of the retaining clips 16.

The cover 14, as best shown in FIG. 2, has a generally concave interior surface 36 and a convex outer surface 38. Side cover walls 40 extend the length of cover 14 in the plane perpendicular to the axis of hinge 24 and end cover walls 41 extend the width of cover 14 in the plane parallel to the axis of hinge 24. Securing recesses 42 are cut in a substantially semi-circular shape from the side cover walls 40 so that when the cover 14 is closed over the anchor plate 12 the securing recesses 42 fit over the restrained tubing to protect and further secure the tubing. The securing recesses 42 operate in conjunction with rim openings 31 to permit the secured tubing to pass unobstructed from the retaining device.

Figure 3:
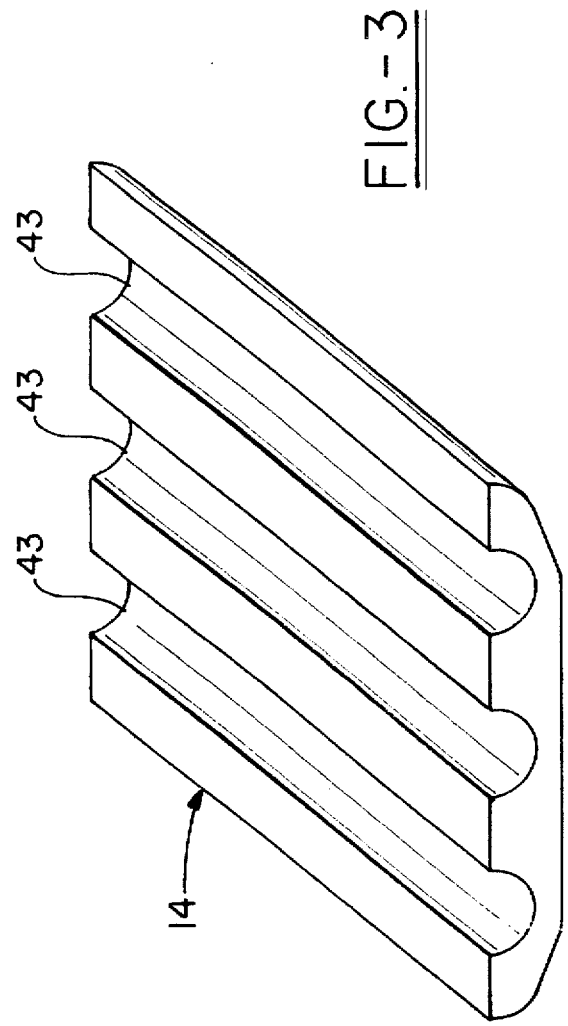
FIG. 3 is a view of one embodiment of the cover 14 of the device showing channels cut out of the body of the cover.

In an alternative embodiment, shown in FIG. 3, the securing recesses 42 are connected by a plurality of channels 43. In such an embodiment, the cover 14 is a solid body with the channels 43 cut out of the body and connecting the opposed securing recesses 42. When the cover 14 is placed in opposed juxtaposition over anchor plate 12 and retaining clips 16 the channels would serve to restrict inadvertent expansion of the retaining clips 16 and the corresponding release of tubing.

The anchor plate rim 29 forms a ledge over which cover 14 can firmly fit, the side cover walls 40 and end cover walls 41 resting on the inner surface 28 of anchor plate 12 when closed. The clamshell type configuration of the cover 14 and anchor plate 12 is held in its closed position by a snap-fit latch and catch configuration. The latch is comprised of an engaging lip 22 protruding from the inner surface 36 of cover 14 and the catch is comprised of an engaging hole 20 in the outer periphery of anchor plate rim 29. It should be clear to those of skill in the art that other variations of a latch and catch-type mechanism may be used to hold the device in its closed position as well as other locking and holding means.

A means for maintaining the restraining device in a convenient position on the patient's body can be introduced through holes 18 in anchor plate 12. In a preferred embodiment, a chain 19 is passed through holes 18 and the device is hung about a patient's neck as a necklace. In an alternative embodiment, the device is pinned or clipped to the patient's garment like a badge such as by passing the appropriate portions of a pin through the holes 18. Or by otherwise attaching a pin 21 to the outer surface 30 of anchor plate 12. Less desirably, an adhesive layer could be secured to the outer surface of the device and correspondingly attached to the patient's body or garment. As described above, the device is particularly adapted to positioning intravenous tubing for total parenteral nutrition (TPN) and other techniques for the intravenous administration of highly concentrated solutions by way of the subclavian vein.

The materials used in the construction of the device are preferably polymeric. Although a number of materials known to those skilled in the art may be used to accomplish the desired construction, the preferred material for the resilient and compressible retaining clips is DELRIN, while the preferred material for the anchor plate 12 and cover 14 is polypropylene. It is envisioned that the device will be formed by injection molding, although other methods of forming the device known in the art are contemplated as well. Unlike previous devices disclosed in the prior art which utilize absorbent materials in their construction, the present invention may be cleaned, sterilized or sanitized and reused if desired.

Although the preferred embodiment of the invention has been described in the foregoing DETAILED DESCRIPTION OF THE PREFERRED EMBODIMENT and illustrated in the accompanying drawings, it will be understood that the invention is not limited to the embodiments disclosed, but is capable of numerous rearrangements, modifications and substitutions of parts and elements without departing from the spirit and scope of the invention.

What is claimed is:

1. A device for securing and protecting tubing used with a medical patient comprising an anchor plate having an inner surface and an outer surface;

at least one retaining means attached to said inner surface of said anchor plate for retaining medical tubing in a fixed position;

a cover covering at least a portion of said inner surface of said anchor plate; and a non-adhesive fastening means for positioning said device relative to said patient.

2. The device of claim 1 wherein said retaining means is comprised of a clamping portion and an anchoring portion.

3. The device of claim 2 wherein said anchor plate includes at least one receiver for receiving said anchoring portion of said retaining means.

4. The device of claim 3 wherein said receiver of said anchor plate is a hole which accepts an anchoring portion of said retaining means.

5. The device of claim 4 wherein said anchoring portion of said retaining means is comprised of a plurality of resilient wings in an expanded configuration which compress while passing through said hole and secure said retaining means to said anchor plate by returning to said expanded configuration.

6. The device of claim 2 wherein said tube clamping portion is comprised of a pair of resilient retaining clip arms of predetermined spacing extending substantially perpendicular to said anchor plate for engaging and holding medical tubing.

7. The device of claim 6 wherein said pair of resilient retaining clip arms forms a U-shaped channel for preventing said medical tubing from disengaging from said tube clamping portion.

8. The device of claim 7 further comprising a latching means for maintaining said cover in a closed position over said anchor plate.

9. The device of claim 1 wherein said retaining means comprises a plurality of retaining clips.

10. The device of claim 9 wherein said plurality of retaining clips is color-coded to convey information.

11. The device of claim 9 wherein said latching means is comprised of a latch having a protruding lip and a catch having an opening for engaging said lip.

12. The device of claim 1 wherein said cover is connected to said anchor plate by a hinge providing a means by which said cover is held in opposed juxtaposition to said anchor plate so that when said cover is closed over said anchor plate they form a clamshell-type structure.

13. The device of claim 12, wherein said latch is disposed on said cover and said catch is disposed on said anchor plate or vice versa.

14. The device of claim 1 wherein said cover has a supplemental retaining means for further securing medical tubing.

15. The device of claim 14, wherein said supplemental retaining means is a semicircular recess in said cover, said recess reinforcing said retaining means when said cover is in a closed configuration, by fitting over and restricting a secured tube from disengaging from said retaining means.

16. The device of claim 1 wherein said fastening means is a clip so that the tube restraint is worn as a badge.

17. The device of claim 1 wherein said fastening means is a chain attached to said device and worn as a necklace.

18. The device of claim 1 wherein said fastening means is a pin attached to said device for further attachment to a patient's garment.

19. The device of claim 1 wherein said device is positioned near the subclavian vein.

* * * * *